United States Patent
Kolm et al.

(10) Patent No.: US 11,749,397 B2
(45) Date of Patent: Sep. 5, 2023

(54) INFERRING SEMANTIC DATA ORGANIZATION FROM MACHINE-LEARNED RELATIONSHIPS

(71) Applicant: CERNER INNOVATION, INC., Kansas City, KS (US)

(72) Inventors: Margaret Cushing Kolm, Kanas City, MO (US); Christopher S. Finn, Liberty, MO (US); David P. McCallie, Jr., Stilwell, KS (US)

(73) Assignee: Cerner Innovation, Inc., Kansas City, MO (US)

( * ) Notice: Subject to any disclaimer, the term of this patent is extended or adjusted under 35 U.S.C. 154(b) by 581 days.

(21) Appl. No.: 15/851,389

(22) Filed: Dec. 21, 2017

(65) Prior Publication Data

US 2019/0198154 A1 Jun. 27, 2019

(51) Int. Cl.
*G16H 30/20* (2018.01)
*G06F 16/51* (2019.01)
*G16H 40/63* (2018.01)
*G16H 40/20* (2018.01)
*G16H 10/60* (2018.01)

(52) U.S. Cl.
CPC .............. *G16H 30/20* (2018.01); *G06F 16/51* (2019.01); *G16H 10/60* (2018.01); *G16H 40/20* (2018.01); *G16H 40/63* (2018.01)

(58) Field of Classification Search
CPC ........ G16H 10/00; G16H 50/50; G16H 70/00; G06F 19/30; G06F 16/51; G06Q 50/22–24
See application file for complete search history.

(56) References Cited

U.S. PATENT DOCUMENTS

| 2008/0201280 | A1* | 8/2008 | Martin | G06N 20/00 706/45 |
| 2016/0203281 | A1* | 7/2016 | Zalis | G16H 50/20 705/3 |
| 2018/0089382 | A1* | 3/2018 | Allen | G06F 40/284 |
| 2019/0057774 | A1* | 2/2019 | Velez | G16H 50/50 |

OTHER PUBLICATIONS

Taranath N.L., S. B. Patil, P. Patil and C. K. Subbaraya, "Medical Decision Support System for the missing data using Data mining," 2015 IEEE International Conference on Electrical, Computer and Communication Technologies (ICECCT), 2015, pp. 1-7, doi: 10.1109/ICECCT.2015.7226038 (Year: 2015).*

G. Bucci, V. Sandrucci and E. Vicario, "Ontologies and Bayesian Networks in Medical Diagnosis," 2011 44th Hawaii International Conference on System Sciences, 2011, pp. 1-8, doi: 10.1109/HICSS.2011.333 (Year: 2011).*

* cited by examiner

*Primary Examiner* — Joseph D Burgess
(74) *Attorney, Agent, or Firm* — Invoke (57) ABSTRACT

Systems, methods, and user interfaces infer data organization for display. An inference system learns patterns of how various healthcare items are typically grouped on a display so data can be aggregated and displayed in appropriate groupings to a clinician user. From a user perspective, it appears as though the display has been manually edited or a mapping has been created so that items are displayed in appropriate groups, even though neither editing nor mapping has been performed.

30 Claims, 3 Drawing Sheets

INFERRING SEMANTIC DATA ORGANIZATION FROM MACHINE-LEARNED RELATIONSHIPS

BACKGROUND

Traditionally, a wealth of healthcare data exists with respect to each patient. In an electronic medical record (EMR) this data is represented by many discrete data elements. Many of these are results, identified by a "type" of test or observation, having a value in the form of a number, text, document or other format, and having other attributes describing time, source, authorship. To display these data in a clinically meaningful organization, most EMRs employ pre-built organizations of data types based on commonly accepted groupings related to clinical function. For example, a clinician expects to view lab results together, and to review lab results related to blood cell function (hematology) as a group, including data types Red Blood Cell Count, White Blood Cell Count, Platelet Count, etc. Similarly, vital signs, serum chemistry tests, or diagnostic radiology tests are generally grouped together. Building this organization is a time-consuming task requiring knowledge of medicine, and of all the data element types supported by the particular EMR.

With the increased demand for interoperability of clinical data, EMRs frequently receive clinical data elements in electronic transmissions from other systems, external to the organization. The EMR displays these "outside" data elements to the clinician user of the EMR. These data should assist clinicians in understanding the patient history, and care that has been delivered outside of their institution. Unfortunately, no clinically meaningful display organization exists for these outside data elements. The challenges are many: The type of an outside data element is frequently not identifiable other than by a name and/or a proprietary identifier, making it difficult for a curator to interpret the result type and requiring custom organization for each data source. On the occasion when a data element type is associated to an identifier in a standard nomenclature, manual organization is still necessary, since no display organization exists for standard nomenclatures such as LOINC. The number of data types that might be received is vast, and no catalog is provided; one can only determine the possible data types by examining data already received. Moreover, data types change frequently, as new source systems are added, or source systems add new data elements, or change the naming of previous data types. For all these reasons, manual creation of a meaningful display organization is an immense and challenging task. As a result, most systems organize the display of outside data in ways that do not reflect clinical significance: alphabetically, chronologically, by source system. It is difficult for a clinician to find and interpret data elements. Outside data is under-utilized. Users are frustrated. Healthcare cost is affected when tests are repeated, and the impact can even extend to the quality of care.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present disclosure relate to systems, methods, and user interfaces inferring data organization for display. More particularly, embodiments of the present disclosure learn patterns of how various healthcare items are typically grouped on a display so data can be aggregated and displayed in appropriate groupings to a clinician user. To do so, inferred relations of orders, results, or discrete data within a medical information system are initially identified. The inferred relations of orders, results, or discrete data within the medical information system are utilized to infer a display ontology that groups similar data for presentation to a user.

BRIEF DESCRIPTION OF THE SEVERAL VIEWS OF THE DRAWINGS

The present invention is described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

As noted in the background, a wealth of healthcare data exists with respect to each patient. In an electronic medical record (EMR) this data is represented by many discrete data elements. Many of these are results, identified by a "type" of test or observation, having a value in the form of a number, text, document or other format, and having other attributes describing time, source, authorship. To display these data in a clinically meaningful organization, most EMRs employ pre-built organizations of data types based on commonly accepted groupings related to clinical function. For example, a clinician expects to view lab results together, and to review lab results related to blood cell function (hematology) as a group, including data types Red Blood Cell Count, White Blood Cell Count, Platelet Count, etc. Similarly, vital signs, serum chemistry tests, or diagnostic radiology tests are generally grouped together. Building this organization is a time-consuming task requiring knowledge of medicine, and of all the data element types supported by the particular EMR.

With the increased demand for interoperability of clinical data, EMRs frequently receive clinical data elements in electronic transmissions from other systems, external to the organization. The EMR displays these "outside" data elements to the clinician user of the EMR. These data should assist clinicians in understanding the patient history, and care that has been delivered outside of their institution. Unfortunately, no clinically meaningful display organization exists for these outside data elements. The challenges are many: The type of an outside data element is frequently not identifiable other than by a name and/or a proprietary identifier, making it difficult for a curator to interpret the result type and requiring custom organization for each data source. On the occasion when a data element type is associated to an identifier in a standard nomenclature, manual organization is still necessary, since no display organization exists for standard nomenclatures such as LOINC. The number of data types that might be received is vast, and no catalog is provided; one can only determine the possible data types by examining data already received. Moreover, data types change frequently, as new source systems are added, or source systems add new data elements, or change the naming of previous data types. For all these reasons, manual creation of a meaningful display organization is an immense and challenging task. As a result, most systems organize the display of outside data in ways that do not reflect clinical significance: alphabetically, chronologically, by source system. It is difficult for a clinician to find and interpret data elements. Outside data is under-utilized. Users are frustrated. Healthcare cost is affected when tests are repeated, and the impact can even extend to the quality of care.

Embodiments of the present disclosure relate to systems, methods, and user interfaces inferring data organization for display. More particularly, embodiments of the present disclosure learn patterns of how various healthcare items are typically grouped on a display so data can be aggregated and displayed in appropriate groupings to a clinician user. To do so, inferred relations of orders, results, or discrete data within a medical information system are initially identified. The inferred relations of orders, results, or discrete data within the medical information system are utilized to infer a display ontology that groups similar data for presentation to a user.

Accordingly, one embodiment of the present disclosure is directed to a system for inferring data organization for display. The system includes a processor; and a computer storage medium storing computer-useable instructions that, when used by the processor, causes the processor to: identify inferred relations of orders, results, or discrete data within a medical information system; and utilizing the inferred relations of orders, results, or discrete data within the medical information system, infer a display ontology that groups related data for presentation to a user.

In another embodiment, the present disclosure directed to a computerized method for inferring data organization for display. The method comprises identifying inferred relations of orders, results, or discrete data within a medical information system. The method also comprises utilizing the inferred relations of orders, results, or discrete data within the medical information system to infer a display ontology that groups related data for presentation to a user.

In yet another embodiment, the present disclosure is directed to one or more computer storage media having computer-executable instructions embodied thereon that, when executed by a computer, causes the computer to perform operations to facilitate inferring data organization for display. The operations include identifying inferred relations of orders, results, or discrete data within a medical information system. The operations also include utilizing the inferred relations of orders, results, or discrete data within the medical information system, inferring a display ontology that groups related data for presentation to a user, the display ontology eliminating a need to map which orders, results, or discrete data to specific data types or groups.

Figure 1:
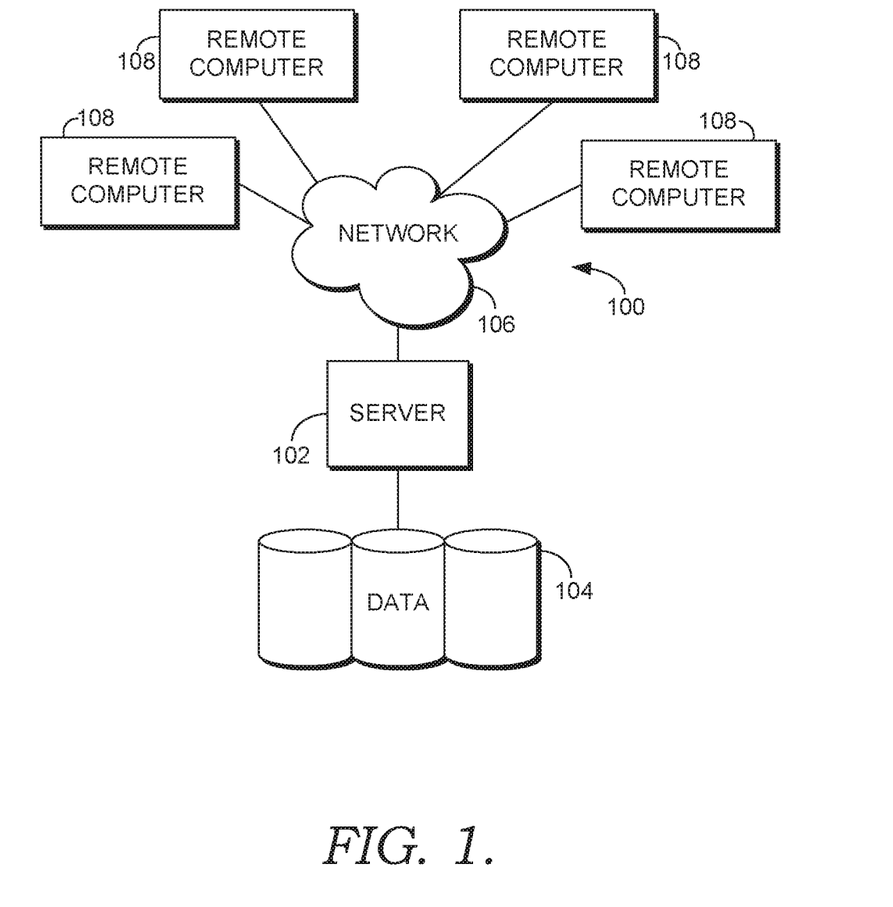
FIG. 1 is a block diagram of an exemplary operating environment suitable to implement embodiments of the present invention.

Having briefly described embodiments of the present invention, an exemplary operating environment suitable for use in implementing embodiments of the present invention is described below. FIG. 1 provides an aspect of an example operating environment with which embodiments of the present invention may be implemented. The aspect of an operating environment is illustrated and designated generally as reference numeral 100.

Example operating environment 100 comprises a general purpose computing device in the form of a control server 102. Exemplary components of the control server 102 comprise a processing unit, internal system memory, and a suitable system bus for coupling various system components, including database cluster 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Control server 102 typically includes therein, or has access to, a variety of computer-readable media, for instance, database cluster 104. Computer-readable media can be any available media that might be accessed by control server 102, and includes volatile and nonvolatile media, as well as, removable and nonremovable media. Computer-readable media might include computer storage media. Computer storage media includes volatile and nonvolatile media, as well as removable and nonremovable media implemented in any method or technology for storage of information, such as computer-readable instructions, data structures, program modules, or other data. In this regard, computer storage media might comprise RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 102. Computer storage media does not comprise signals per se. Combinations of any of the above also may be included within the scope of computer-readable media.

The computer storage media discussed above and illustrated in FIG. 1, including database cluster 104, provide storage of computer-readable instructions, data structures, program modules, and other data for the control server 102. In some embodiments, data cluster 104 takes the form of a cloud-based data store, and in some embodiments is accessible by a cloud-based computing platform.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and providers' offices. Providers may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like.

The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

In some embodiments, remote computers 108 comprise computing-devices that are part of a cloud-computing platform. In some embodiments, a remote computer 108 is associated with a health records, data source such as an electronic health record (EHR) system of a hospital or medical organization, a health information exchange EHR, insurance provider EHR, ambulatory clinic EHR, or patient-sensor, or other data source, and facilitates accessing data of the source and communicating the data to control server 102 and/or other computing devices on a cloud computing platform, including other remote computers 108.

Exemplary computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networked environment, program modules or portions thereof might be stored in association with the control server 102, the database cluster 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

In some embodiments, control server 102 is a computing system or platform made up of one or more computing devices. Embodiments of control server 102 may be a distributed computing system, a centralized computing system, a single computer such as a desktop or laptop computer or a networked computing system. Thus, in some embodiments, control server 102 comprises a multi-agent computer system with software agents.

Figure 2:
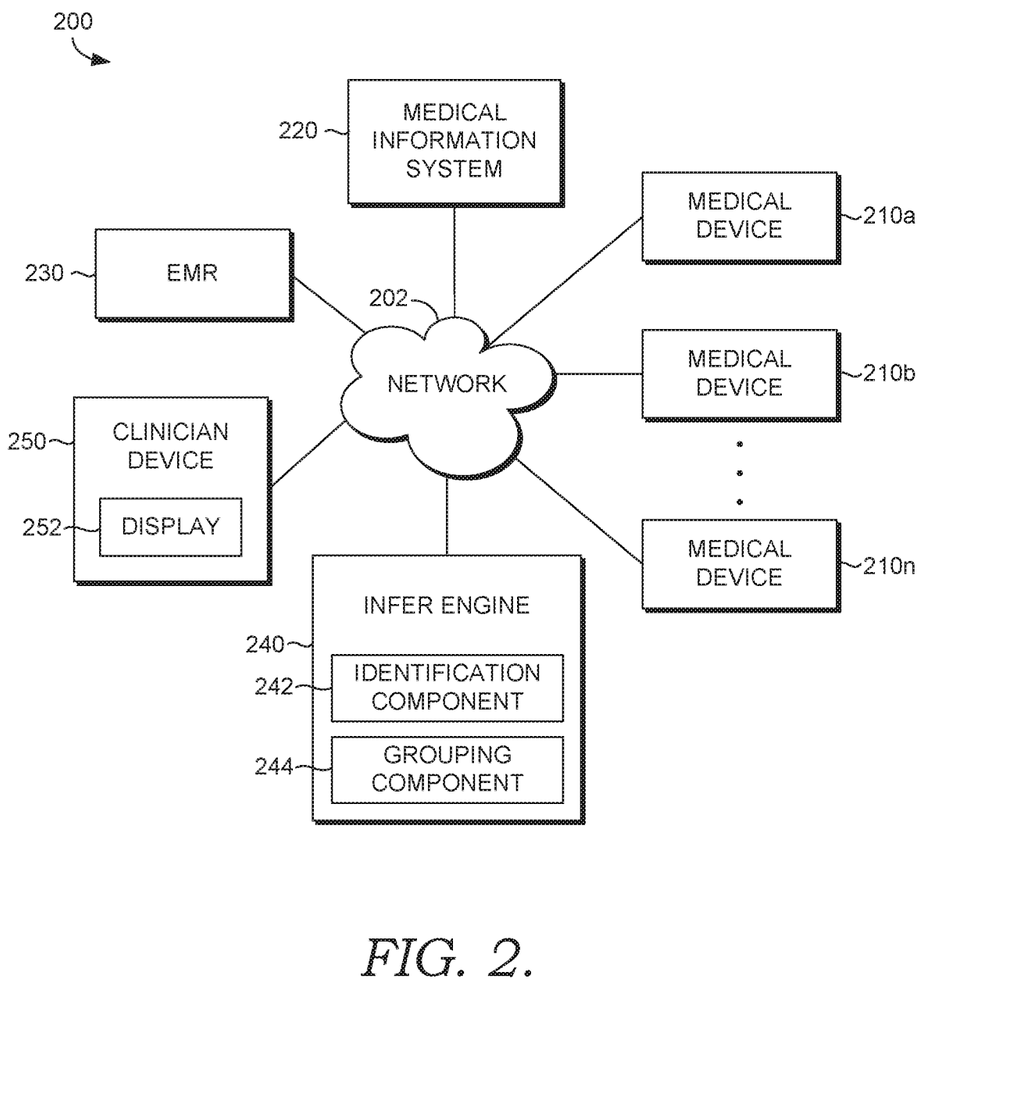
FIG. 2 depicts an exemplary framework of an inference system suitable to implement embodiments of the present invention.

Turning now to FIG. 2, an exemplary framework of an inference system 200 is shown, in accordance with an aspect of the present invention. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory. The inference system 200 may be implemented via any type of computing device, such as computing device 100 described above with reference to FIG. 1, for example.

The inference system 200 generally operates to infer data organization for display. In this way, the inference system 200 learns patterns of how various healthcare items are typically grouped on a display so data can be aggregated and displayed in appropriate groupings to a clinician user. From a user perspective, it appears as though the display has been manually edited or a mapping has been created so that items are displayed in appropriate groups, even though neither editing nor mapping has been performed.

As shown in FIG. 2, the inference system 200 includes, among other components not shown, medical device(s) 210a-210n, a medical information system 220, an electronic medical record 230, an infer engine 240, and a clinician device 250. It should be understood that the inference system 200 shown in FIG. 2 is an example of one suitable computing system architecture. Each of the components shown in FIG. 2 may be implemented via any type of computing device, such as computing device 100 described with reference to FIG. 1, for example.

The components may communicate with each other via a network 202, which may include, without limitation, one or more local area networks (LANs) and/or wide area networks (WANs). Such networking environments are commonplace in offices, enterprise-wide computer networks, intranets, and the Internet. It should be understood that any number of infer engines 240 may be employed within the inference system 200 within the scope of the present disclosure. Each may comprise a single device or multiple devices cooperating in a distributed environment. For instance, the infer engine 240 (or any of its components: identification component 242, grouping component 244) may be provided via multiple devices arranged in a distributed environment that collectively provide the functionality described herein. In other embodiments, a single device may provide the functionality of multiple components of the inference system 200. In some embodiments, some or all functionality provided by the infer engine 240 (or any of its components) may be provided by a user device. Additionally, other components not shown may also be included within the network environment.

Medical device(s) 210a-220n might include cardiac monitors, infusion pumps, balloon pumps, patient beds, sequential-compression devices, electronic security devices, and vital-sign detecting devices. Medical device(s) 210a-210n may generate various data (e.g., measured heart rate) and/or metadata that, as described in more detail below, is communicated to other components (e.g., medical information system 220, EMR 230, or clinician device 250) of operating environment 200.

Medical information system 220 includes an integrated system of healthcare-related information that is usable by a healthcare facility to operate and provide patient care. For example, healthcare information system 220 includes an electronic medical record 230 (also referred to herein as "EMR"). EMR 230 includes an electronic version of patient records including information for the patient, such as surveys, trauma documentation, including images, clinical notes, orders, summaries, reports, analyses, information received from medical devices 210a-210n, infer engine 240, and/or clinician device 250 or other types of electronic medical documentation relevant to a particular patient's condition and/or treatment. Electronic clinical documents contain various types of information relevant to the condition and/or treatment of a particular patient and can include information relating to, for example, patient identification information, images, alert history, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, clinician assignments, and a host of other relevant clinical information. The content and volume of such information in the EMR 230 is not intended to limit the scope of embodiments of the present invention in any way.

Clinician device 250 may be any type of computing device used within a healthcare facility to receive, display, and send information to a user, such as a clinician. Clinician device 250 may be capable of communicating via the network 202 with medical device(s) 210a-210n, medical information system 220, EMR 230, and/or infer engine 240. Such devices may include any type of mobile and portable devices including cellular telephones, personal digital assistants, tablet PCs, smart phones, and the like.

Clinician device 250 is configured to display information to a clinician via a display 252. The information may include communications initiated by and/or received by the infer engine 240. Embodiments are not intended to be limited to visual display but rather may also include audio presentation, visual presentation, combined audio/visual presentation, and the like.

The infer engine 210 is generally configured to receive information from each of the medical device(s) 210a-210n, medical information system 220, EMR 230, and clinician device 250. As described above, the infer engine 210 includes several components including a an identification component 242 and a grouping component 244. The identification component 242 and the grouping component 244 utilize information received from the medical device(s) 210a-210n, medical information system 220, EMR 230, and/or clinician device 250 to learn patterns of how various healthcare items are typically grouped on a display so data can be aggregated and displayed in appropriate groupings to a clinician user.

Generally, identification component 242 identifies inferred relations of orders, results, or discrete data within a medical information system. The discrete data may be communicated in a Health Level-7 data format and may comprise a type, a value, units, source information, order number, ordering physician, workflow tracking concepts, range of normal, or a flag to indicate abnormal. The orders, results, or discrete data may include metadata. The metadata may identify a source, a date, a time, a specimen, identifiers relating to originating workflow, classification, originating location or organization, originating system, order number, workflow tracking concepts, or personnel involved in the production of a data element corresponding to the orders, results, or discrete data. The metadata may also include a Logical Observation Identifiers Names and Codes ("LOINC").

Identification component 242 may utilize the metadata to identify which orders, results, or discrete data may have been ordered by the same clinician, on the same date, at the same time, from the same sample, or from the same specimen. Such inferred relations within the metadata may indicate to the identification component 242 that a clinician viewing the orders, results, or discrete data may wish to view the orders, results, or discrete data as part of a group. Identification component 242 may utilize various machine learning algorithms to learn when certain inferred relations are meaningful, indicating the orders, results, or discrete data or when they can be ignored.

Grouping component 244 generally, utilizes the inferred relations of the orders, results, or discrete data within the medical information system, inferring a display ontology that groups similar data for presentation to a user. The display ontology eliminates a need to map which orders, results, or discrete data belongs in a particular group. Thus, after identification component 242 has identified inferred relations of the orders, results, or discrete data, grouping component 244 may utilize various machine learning algorithms to determine how to group data that is similar (i.e., identified inferred relations). In this way, grouping component 244 learns patterns of how data is grouped so when results are displayed, they are displayed with the inferred display ontology.

For example, certain labs may be frequently ordered together. Information in one lab may be relevant to information in another lab. However, such relevance may not be readily assimilated unless the labs are viewed as part of a group. In another example, a number of discrete results are often available from a CBC. Grouping component 244 prevents the results from merely being displayed alphabetically and groups the results from the CBC together so the clinician is able to assimilate that a CBC was ordered and quickly identify the results.

Consider a small hypothetical sample of clinical data shown below in Table 1, including laboratory results for blood chemistry and hematology, and vital signs and measurements recorded in patient care:

TABLE 1

| Patient | Type | Date | Provider | Tracking ID | Source System | Context |
|---|---|---|---|---|---|---|
| 1 | Sodium | 1 May 0800 | Terry Parker, MD | 1234 | CMHPath | CMH Lab |
| 1 | Potassium | 1 May 0800 | Terry Parker, MD | 1234 | CMHPath | CMH Lab |
| 1 | CO2 | 1 May 0800 | Terry Parker, MD | 1234 | CMHPath | CMH Lab |
| 1 | Chloride | 1 May 0800 | Terry Parker, MD | 1234 | CMHPath | CMH Lab |
| 1 | Systolic BP | 1 May 0830 | J. Doe RN | 123034-BP | Care Net | MemHospInpt |
| 1 | Diastolic BP | 1 May 0830 | J. Doe RN | 123034-BP | Care Net | MemHospInpt |
| 2 | BUN | 1 May 0815 | Terry Parker, MD | 456 | CMHPath | CMH Lab |

TABLE 1-continued

| Patient | Type | Date | Provider | Tracking ID | Source System | Context |
|---|---|---|---|---|---|---|
| 2 | Creatine | 1 May 0815 | Terry Parker, MD | 456 | CMHPath | CMH Lab |
| 3 | Systolic BP | 1 May 0910 | J. Doe RN | | Care Net | MemHospInpt |
| 3 | Diastolic BP | 1 May 0910 | J. Doe RN | | Care Net | MemHospInpt |
| 3 | Sodium | 1 May 1020 | Pat Brown, MD | 789 | CMHPath | CMH Lab |
| 3 | Potassium | 1 May 1020 | Pat Brown, MD | 789 | CMHPath | CMH Lab |
| 3 | CO2 | 1 May 1020 | Pat Brown, MD | 789 | CMHPath | CMH Lab |
| 3 | Chloride | 1 May 1020 | Pat Brown, MD | 789 | CMHPath | CMH Lab |
| 3 | BUN | 1 May 1020 | Pat Brown, MD | 789 | CMHPath | CMH Lab |
| 3 | Creatine | 1 May 1020 | Pat Brown, MD | 789 | CMHPath | CMH Lab |
| 3 | glucose | 1 May 1020 | Pat Brown, MD | 789 | CMHPath | CMH Lab |
| 3 | calcium | 1 May 1020 | Pat Brown, MD | 789 | CMHPath | CMH Lab |
| 4 | hemoglobin | 1 May 1512 | Terry Parker, MD | 444555 | CMHPath | CMH Lab |
| 4 | hematocrit | 1 May 1512 | Terry Parker, MD | 444555 | CMHPath | CMH Lab |
| 5 | Sodium | 1 May 1810 | Pat Brown, MD | 789 | CMHPath | CMH Lab |
| 5 | Potassium | 1 May 1810 | Pat Brown, MD | 789 | CMHPath | CMH Lab |
| 5 | CO2 | 1 May 1810 | Pat Brown, MD | 789 | CMHPath | CMH Lab |
| 5 | Chloride | 1 May 1810 | Pat Brown, MD | 789 | CMHPath | CMH Lab |
| 5 | Systolic BP | 1 May 1945 | B. Smith RN | | CareNet | MemHospInpt |
| 5 | Diastolic BP | 1 May 1945 | B. Smith RN | | CareNet | MemHospInpt |
| 5 | Temperature | 1 May 1945 | B. Smith RN | | CareNet | MemHospInpt |
| 5 | Pulse | 1 May 1945 | B. Smith RN | | CareNet | MemHospInpt |
| 6 | hemoglobin | 1 May 1950 | Terry Parker, MD | 9876 | CMHPath | CMH Lab |
| 6 | hematocrit | 1 May 1950 | Terry Parker, MD | 9876 | CMHPath | CMH Lab |
| 6 | RBC | 1 May 1950 | Terry Parker, MD | 9876 | CMHPath | CMH Lab |
| 6 | WBC | 1 May 1950 | Terry Parker, MD | 9876 | CMHPath | CMH Lab |
| 6 | Platelet | 1 May 1950 | Terry Parker, MD | 9876 | CMHPath | CMH Lab |

The serum electrolyte results, "Sodium" and "Potassium," are typically ordered and performed together. Consequently, most instances of these tests share attributes such as date (of blood draw), source system, tracking number, performing location. Other blood chemistry tests, such as "BUN", frequently share characteristics such as performing location with electrolytes, and are performed together in many instances (e.g., when a full Basic Metabolic Panel is requested). Hematology tests, including "hematocrit" and "RBC" (red blood cell count) often originate in the same laboratory location, but share fewer attributes with electrolytes. "Systolic blood pressure" and other vital signs have little metadata correlation with electrolytes.

By applying machine learning techniques, such as those described below, correlation between data types and distance measures can be calculated calculated. A small sample of these inferred relations is shown below in Table 2:

TABLE 2

| | Diastolic BP | hematocrit | hemoglobin | Potassium | RBC | Sodium | Systolic BP | Temperature | WBC | |
|---|---|---|---|---|---|---|---|---|---|---|
| BUN | 0.832 | 0.386 | 0.386 | 0.247 | 0.756 | 0.756 | 0.832 | 0.876 | 0.765 | BUN |
| Diastolic BP | | 0.883 | 0.883 | 0.814 | 0.912 | 0.814 | 0.001 | 0.134 | 0.912 | Diastolic BP |
| hematocrit | | | 0.156 | 0.356 | 0.796 | 0.354 | 0.876 | 0.892 | 0.796 | hematocrit |
| hemoglobin | | | | 0.356 | 0.798 | 0.354 | 0.883 | 0.898 | 0.798 | hemoglobin |
| Potassium | | | | | 0.692 | 0.032 | 0.814 | 0.856 | 0.694 | Potassium |
| RBC | | | | | | 0.654 | 0.914 | 0.956 | 0.045 | RBC |
| Sodium | | | | | | | 0.814 | 0.856 | 0.673 | Sodium |
| Systolic BP | | | | | | | | 0.134 | 0.914 | Systolic BP |
| Temperature | | | | | | | | | 0.956 | Temperature |

The grouping component 244 may utilize the distance measures to create an organization of result types. In embodiments, this may be done by relations alone or augmented by manual content. Augmentation can include mapping into a template framework and manual adjustment of the final organization.

To create an organization from inferred relations, the algorithm starts by creating clusters of the most closely related data types. "Systolic BP" and "Diastolic BP" are clustered together, as are "Sodium" and "Potassium". Each additional data type is added into the organization, in the position that maximally corresponds proximity to the inferred distance measure for each data type. Frequency of occurrence may be used as a tie-breaker, with more common data types appearing nearer the top of the list. An exemplary resulting organization is illustrated in Table 3 below:

TABLE 3

Chloride
CO2
Potassium
Sodium
BUN
Creatinine
Calcium
Glucose

TABLE 3-continued

Hematocrit
Hemoglobin
Platelet
RBC
WBC
Diastolic BP
Systolic BP

TABLE 3-continued

Temperature
Pulse

As illustrated in Table 4 with annotations below, As seen with annotations below, the resulting organization groups data types according to common clinical categorization:

TABLE 4

| | | |
|---|---|---|
| Potassium | Electrolytes | Chemistry/Basic Metabolic Panel |
| Sodium | | |
| Chloride | | |
| CO2 | | |
| BUN | Kidney function | |
| Creatinine | | |
| Calcium | Other blood chemistry | |
| Glucose | | |
| Hematocrit | | Hematology |
| Hemoglobin | | |
| Platelet | CBC | |
| RBC | | |
| WBC | | |
| Diastolic BP | Blood Pressure | Vital Signs |
| Systolic BP | | |
| Temperature | | |
| Pulse | | |

As noted, the identification component 242 and the grouping component 244 may utilize one or more machine learning algorithms to determine which items may be related (i.e., co-occurring) and how items should be displayed as part of a group. For example, an ensemble of alternating decision trees can be used to determine when information received from the medical device(s) 210a-210n, medical information system 220, EMR 230, and/or clinician device 250 is related and should be displayed as part of a group. Each decision tree may be trained on a random subset of instances and features of the healthcare data. In some embodiments, the number of decision trees used is based on the type of healthcare data received or specific information pertaining to the patient.

A generic decision tree is a decision support tool which arrives at a decision after following steps or rules along a tree-like path. While most decision trees are only concerned about the final destination along the decision path, alternating decision trees take into account every decision made along the path and may assign a score for every decision encountered. Once the decision path ends, the algorithm sum all of the incurred scores to determine a final classification (i.e., information that should be grouped and displayed together). In some embodiments, the alternating decision tree algorithm may be further customized. For example, the alternating decision tree algorithm may be modified by wrapping it in other algorithms.

A machine learning algorithm may use a generic cost matrix. The intuition behind the cost matrix is as follows. If the model predicts a member to be classified in group A, and the member really should be in group A, no penalty is assigned. However, if this same member is predicted to be in group B, C, or D, a 1-point penalty will be assigned to the model for this misclassification, regardless of which group the member was predicted to be in. Thus, all misclassifications are penalized equally. However, by adjusting the cost matrix, penalties for specific misclassifications can be assigned. For example, where someone who was truly in group D was classified in group A, the model could increase the penalty in that section of the cost matrix. A cost matrix such as this may be adjusted as needed to help fine tune the model for different iterations, and may be based on the specific patient in some embodiments.

With regards to a multi-class classifier, some machine learning algorithms, such as alternating decision trees, generally only allow for the classification into two categories (e.g. a binary classification). In cases where it is desired to classify three or more categories, a multi-class classifier is used.

In order to assist the alternating decision tree in selecting best features for predictive modeling, an ensemble method called rotation forest may be used. The rotation forest algorithm randomly splits the dataset into a specified number of subsets and uses a clustering method called Principal Component Analysis to group features deemed useful. Each tree is then gathered (i.e., "bundled into a forest") and evaluated to determine the features to be used by the base classifier.

Various alternative classifiers may be used to provide the medical and preventive healthcare personal assistant services. Indeed, there are thousands of machine learning algorithms, which could be used in place of, or in conjunction with, the alternating decision tree algorithm. For example, one set of alternative classifiers comprise ensemble methods.

Ensemble methods use multiple, and usually random, variations of learning algorithms to strengthen classification performance. Two of the most common ensemble methods are bagging and boosting. Bagging methods, short for "bootstrap aggregating" methods, develop multiple models from random subsets of features from the data ("bootstrapping"), assigns equal weight to each feature, and selects the best-performing attributes for the base classifier using the aggregated results. Boosting, on the other hand, learns from the data by incrementally building a model, thereby attempting to correct misclassifications from previous boosting iterations.

Regression models are frequently used to evaluate the relationship between different features in supervised learning, especially when trying to predict a value rather than a classification. However, regression methods are also used with other methods to develop regression trees. Some algorithms combine both classification and regression methods; algorithms that used both methods are often referred to as CART (Classification and Regression Trees) algorithms.

Bayesian statistical methods are used when the probability of some events happening are, in part, conditional to other circumstances occurring. When the exact probability of such events is not known, maximum likelihood methods are used to estimate the probability distributions. A textbook example of Bayesian learning is using weather conditions, and whether a sprinkler system has recently gone off, to determine whether a lawn will be wet. However, whether a homeowner will turn on their sprinkler system is influenced, in part, to the weather. Bayesian learning methods, then, build predictive models based on calculated prior probability distributions.

Another type of classifiers comprise artificial neural networks. While typical machine learning algorithms have a pre-determined starting node and organized decision paths, the structure of artificial neural networks are less structured. These algorithms of interconnected nodes are inspired by the neural paths of the brain. In particular, neural network methods are very effective in solving difficult machine learning tasks. Much of the computation occurs in "hidden" layers.

By way of example and not limitation, other classifiers and methods that may be utilized include (1) decision tree classifiers, such as: C4.5—a decision tree that first selects features by evaluating how relevant each attribute is, then using these attributes in the decision path development; Decision Stump—a decision tree that classifies two categories based on a single feature (think of a single swing of an axe); by itself, the decision stump is not very useful, but becomes more so paired with ensemble methods; LADTree—a multi-class alternating decision tree using a LogitBoost ensemble method; Logistic Model Tree (LMT)—a decision tree with logistic regression functions at the leaves; Naive Bayes Tree (NBTree)—a decision tree with naive Bayes classifiers at the leaves; Random Tree—a decision tree that considers a pre-determined number of randomly chosen attributes at each node of the decision tree; Random Forest—an ensemble of Random Trees; and Reduced-Error Pruning Tree (REPTree)—a fast decision tree learning that builds trees based on information gain, then prunes the tree using reduce-error pruning methods; (2) ensemble methods such as: AdaBoostM1—an adaptive boosting method; Bagging—develops models using boot-strapped random samples, then aggregates the results and votes for the most meaningful features to use in the base classifier; LogitBoost—a boosting method that uses additive logistic regression to develop the ensemble; Multi-BoostAB—an advancement of the AdaBoost method; and Stacking—a method similar to boosting for evaluating several models at the same time; (3) regression methods, such as Logistic Regression—regression method for predicting classification; (4) Bayesian networks, such as BayesNet—Bayesian classification; and NaiveBayes—Bayesian classification with strong independence assumptions; and (4) artificial neural networks such as MultiLayerPerception—a forward-based artificial neural network.

Figure 3:
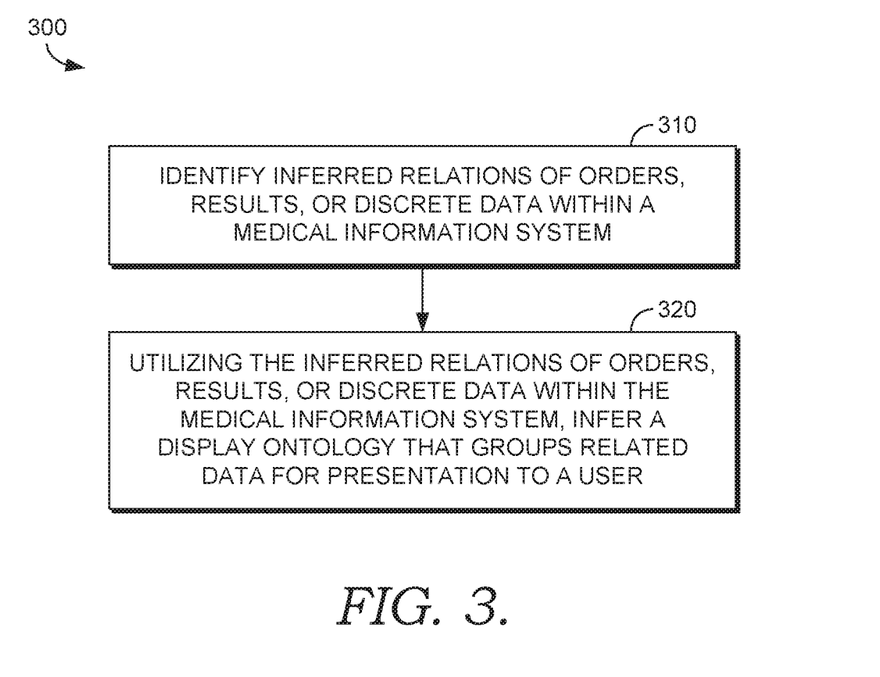
FIG. 3 is a flow diagram of a method for inferring data organization for display, in accordance with embodiments of the invention.

Turning now to FIG. 3, a flow diagram is provided illustrating a method 300 for inferring data organization for display, in accordance with embodiments of the present invention. Method 300 may be performed by any computing device (such as computing device described with respect to FIG. 1) with access to an inference system (such as the one described with respect to FIG. 2) or by one or more components of the inference system.

Initially, at step 310, inferred relations of orders, results, or discrete data within a medical information system are identified. The discrete data may be communicated in a Health Level-7 data format and may comprise a type, a value, units, range of normal, or a flag to indicate abnormal. The orders, results, or discrete data may include metadata. The metadata may identify a source, a date, a time, a specimen, identifiers relating to originating workflow, classification, originating location or organization, originating system, order number, workflow tracking concepts, or personnel involved in the production of a data element corresponding to the orders, results, or discrete data. The metadata includes data type that might be identified by a one or more values from a standard clinical nomenclature, such as LOINC or Systematized Nomenclature of Medicine—Clinical Terms (SNOMED CT).

At step 320, the inferred relations of orders, results, or discrete data within the medical information system are used to create a display ontology that groups similar data for presentation to a user. The display ontology eliminates a need to map which orders, results, or discrete data belongs in a particular group.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A system comprising a processor and a computer storage medium storing computer-useable instructions that, when used by the processor, cause the processor to initiate operations comprising:
   training a machine learning (ML) algorithm based on a subset of instances or features associated with clinical data elements to partition the clinical data elements into multiple groups for display based on historical usage of the clinical data elements for display, the clinical data elements corresponding to orders, results, or discrete data within a medical information system;
   receiving, at a device associated with an electronic interface and the processor of the system, a target set of clinical data elements;
   applying the trained ML algorithm to data associated with the target set of clinical data elements to partition multiple clinical data elements, in the target set of clinical data elements, into a plurality of groups corresponding to a display ontology; and
   initiating presentation of one or more groups, of the plurality of groups, at the electronic interface in accordance with the display ontology.

2. The system of claim 1, wherein the orders, results, or discrete data includes metadata associated with a workflow tracking concept, originating workflow, classification, originating location or organization, originating system, or order number.

3. The system of claim 2, wherein the metadata identifies a source, a date, a time, a specimen, or personnel involved in production of a data element corresponding to the orders, results, or discrete data.

4. The system of claim 1, wherein the discrete data comprises an attribute type, value, units, range of normal, or flag to indicate abnormal.

5. The system of claim 1, wherein the orders, results, or discrete data includes metadata comprises a data type identified by a value from a standard clinical nomenclature, such as Logical Observation Identifiers Names and Codes (LOINC) or Systematized Nomenclature of Medicine—Clinical Terms (SNOMED CT).

6. The system of claim 1, wherein:
   the discrete data is communicated in a Health Level-7 (HL7) standard data format; and
   the target set of clinical data elements includes a particular data element corresponding to the HL7 standard and indicating a patient.

7. A computerized method for inferring data organization for display, the method comprising:
   training a machine learning (ML) algorithm based on a subset of instances or features associated with clinical data elements to partition the clinical data elements into multiple groups for display based on historical usage of the clinical data elements for display, the clinical data elements corresponding to orders, results, or discrete data within a medical information system;

receiving, at a device associated with an electronic interface and the processor of the system, a target set of clinical data elements;

applying the trained ML algorithm to data associated with the target set of clinical data elements to partition multiple clinical data elements, in the target set of clinical data elements, into a plurality of groups corresponding to a display ontology; and initiating presentation of one or more groups, of the plurality of groups, at the electronic interface in accordance with the display ontology.

8. The method of claim 7, wherein the orders, results, or discrete data includes metadata associated with a workflow tracking concept, originating workflow, classification, originating location or organization, originating system, or order number.

9. The method of claim 8, wherein the metadata identifies a source, a date, a time, a specimen, or personnel involved in production of a data element corresponding to the orders, results, or discrete data.

10. The method of claim 7, wherein the discrete data comprises an attribute type, value, units, range of normal, or flag to indicate abnormal.

11. The method of claim 7, wherein the orders, results, or discrete data includes metadata comprises a data type identified by a value from a standard clinical nomenclature, such as Logical Observation Identifiers Names and Codes (LOINC) or Systematized Nomenclature of Medicine—Clinical Terms (SNOMED CT).

12. The method of claim 7, wherein:
the discrete data is communicated in a Health Level-7 (HL7) standard data format; and
the target set of clinical data elements includes a particular data element corresponding to the HL7 standard and indicating a patient.

13. One or more computer storage media having computer-executable instructions embodied thereon that, when executed by a computer, causes the computer to perform operations to facilitate inferring data organization for display, the operations comprising:

training a machine learning (ML) algorithm based on a subset of instances or features associated with clinical data elements to partition the clinical data elements into multiple groups for display based on historical usage of the clinical data elements for display, the clinical data elements corresponding to orders, results, or discrete data within a medical information system;

receiving, at a device associated with an electronic interface and the processor of the system, a target set of clinical data elements;

applying the trained ML algorithm to data associated with the target set of clinical data elements to partition multiple clinical data elements, in the target set of clinical data elements, into a plurality of groups corresponding to a display ontology; and initiating presentation of one or more groups, of the plurality of groups, at the electronic interface in accordance with the display ontology.

14. The one or more media of claim 13, wherein the orders, results, or discrete data includes metadata associated with a workflow tracking concept, originating workflow, classification, originating location or organization, originating system, or order number.

15. The one or more media of claim 14, wherein the metadata identifies a source, a date, a time, a specimen, or personnel involved in production of a data element corresponding to the orders, results, or discrete data.

16. The one or more media of claim 13, wherein the discrete data comprises an attribute type, value, units, range of normal, or flag to indicate abnormal.

17. The one or more media of claim 13, wherein the orders, results, or discrete data includes metadata comprises a data type identified by a value from a standard clinical nomenclature, such as Logical Observation Identifiers Names and Codes (LOINC) or Systematized Nomenclature of Medicine—Clinical Terms (SNOMED CT).

18. The one or more media of claim 13, wherein:
the discrete data is communicated in a Health Level-7 (HL7) standard data format; and
the target set of clinical data elements includes a particular data element corresponding to the HL7 standard and indicating a patient.

19. The system of claim 1, wherein:
training the ML algorithm to partition the clinical data elements into multiple groups for display is based further on previous display groupings; and
the display ontology is configured to (a) eliminate a need to map the target set of clinical data elements to specific data types or groups and (b) reflect a clinical significance among the target set of clinical data elements.

20. The system of claim 1, wherein the ML algorithm is associated with a trained artificial neural network.

21. The system of claim 20, wherein the trained artificial neural network is utilized to learn if certain inferred relations are meaningful, indicating the orders, results, or discrete data or if they can be ignored.

22. The system of claim 1, wherein the orders, results, or discrete data correspond to a particular data element.

23. The system of claim 22, wherein the particular data element indicates a patient.

24. The system of claim 22, wherein the particular data element corresponds to a Health Level-7 (HL7) standard data format and indicates a patient.

25. The system of claim 1, wherein the electronic interface is configured to present the one or more groups via an audio presentation, a visual presentation, or a combined audio/visual presentation.

26. The system of claim 1, wherein at least a portion of the orders, results, or discrete data is received from a medical device, an electronic medical record, or a clinician device.

27. The system of claim 26, wherein the orders, results, or discrete data correspond to a particular treatment or procedure associated with a particular patient, and wherein the operations further comprise initiating the particular treatment or procedure for the particular patient.

28. The system of claim 1, wherein the operations further comprise: training the machine learning (ML) algorithm based on a subset of instances or features associated with additional clinical data elements.

29. The method of claim 7, wherein the orders, results, or discrete data correspond to a particular treatment or procedure associated with a particular patient, and further comprising initiating the particular treatment or procedure for the particular patient.

30. The method of claim 7, wherein the ML algorithm is associated with an artificial neural network, and further comprising training the artificial neural network based on a subset of instances or features associated with additional clinical data elements.

* * * * *